(12) United States Patent
Aaltonen et al.

(10) Patent No.: US 11,432,777 B2
(45) Date of Patent: Sep. 6, 2022

(54) SPORTS APPARATUS FOR PROVIDING INFORMATION

(71) Applicant: Aboense Oy, Turku (FI)

(72) Inventors: Juho Aaltonen, Turku (FI); Hugo Leppäsyrjä, Espoo (FI)

(73) Assignee: Aboense Oy, Turku (FI)

( * ) Notice: Subject to any disclaimer, the term of this patent is extended or adjusted under 35 U.S.C. 154(b) by 927 days.

(21) Appl. No.: 16/155,283

(22) Filed: Oct. 9, 2018

(65) Prior Publication Data

US 2019/0232147 A1 Aug. 1, 2019

Related U.S. Application Data

(63) Continuation-in-part of application No. 15/492,372, filed on Apr. 20, 2017, now abandoned.

(30) Foreign Application Priority Data

May 6, 2016 (FI) ..................................... 20165390

(51) Int. Cl.
*A63B 71/06* (2006.01)
*A61B 5/024* (2006.01)
(Continued)

(52) U.S. Cl.
CPC .............. *A61B 5/742* (2013.01); *A61B 5/024* (2013.01); *A61B 5/02416* (2013.01); *A61B 5/02438* (2013.01); *A61B 5/1118* (2013.01); *A61B 5/6803* (2013.01); *A61B 5/6815* (2013.01); *A61B 5/6895* (2013.01); *A63B 24/0062* (2013.01); *A63B 71/0622* (2013.01); *G01C 22/006* (2013.01); *A61B 2503/10* (2013.01); *A61B 2505/09* (2013.01);
(Continued)

(58) Field of Classification Search
None
See application file for complete search history.

(56) References Cited

U.S. PATENT DOCUMENTS 10,391,361 B2 * 8/2019 Watterson .......... A63B 71/0622
2003/0018274 A1 * 1/2003 Takahashi ............ A61B 5/0059
600/500

(Continued)

FOREIGN PATENT DOCUMENTS

CN 107636657 A * 1/2018 ............. G03B 29/00
EP 1134555 A1 * 9/2001 ............ G01C 22/006

*Primary Examiner* — Angela M Hoffa
*Assistant Examiner* — Younhee Choi
(74) *Attorney, Agent, or Firm* — Ziegler IP Law Group, LLC

(57) ABSTRACT

A device for generating a projected image based on an activity related parameter includes a first sensor for detecting the activity related parameter, a second sensor for detecting an orientation of the device, a processor coupled to the first sensor for creating information from the detected activity related parameter, a light source for emitting a light beam from the device to project the created information as an image onto a surface outside the device and at least a first actuator for adjusting a relative direction of the light beam with respect to the detected orientation of the device. The surface outside the device is a ground surface and a distance between the device and the projected image is a function of the detected activity related parameter.

20 Claims, 14 Drawing Sheets

(51) Int. Cl.
*A63B 24/00* (2006.01)
*A61B 5/11* (2006.01)
*G01C 22/00* (2006.01)
*G09B 19/00* (2006.01)
*A61B 5/00* (2006.01)

(52) U.S. Cl.
CPC .......... *A61B 2562/0219* (2013.01); *A63B 2071/0658* (2013.01); *A63B 2220/40* (2013.01); *A63B 2220/803* (2013.01); *A63B 2220/833* (2013.01); *A63B 2220/836* (2013.01); *A63B 2225/50* (2013.01); *A63B 2225/74* (2020.08); *A63B 2230/062* (2013.01); *G09B 19/0038* (2013.01)

(56) References Cited

U.S. PATENT DOCUMENTS

| | | | | |
|---|---|---|---|---|
| 2003/0184575 | A1* | 10/2003 | Reho | G06F 1/163 715/714 |
| 2007/0106172 | A1* | 5/2007 | Abreu | A61B 8/0808 600/549 |
| 2009/0005961 | A1* | 1/2009 | Grabowski | G02B 27/01 701/532 |
| 2015/0379351 | A1* | 12/2015 | Dibenedetto | H04N 5/44504 345/633 |

* cited by examiner

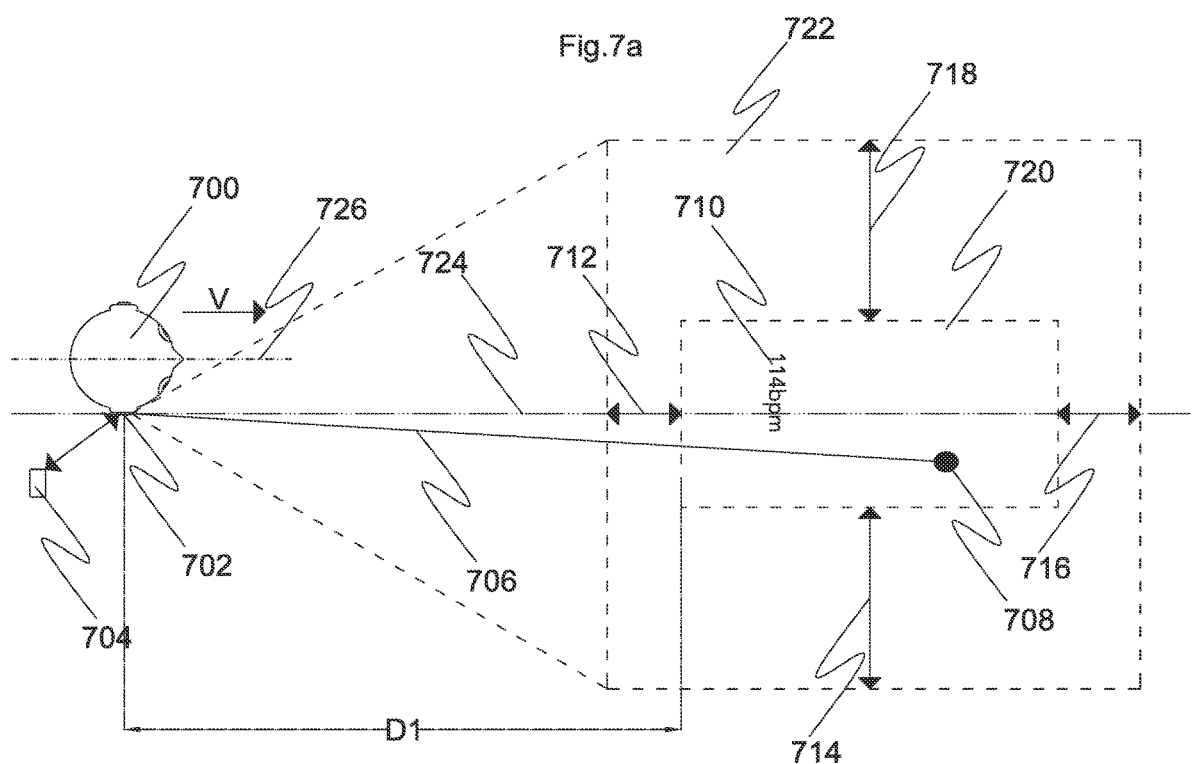

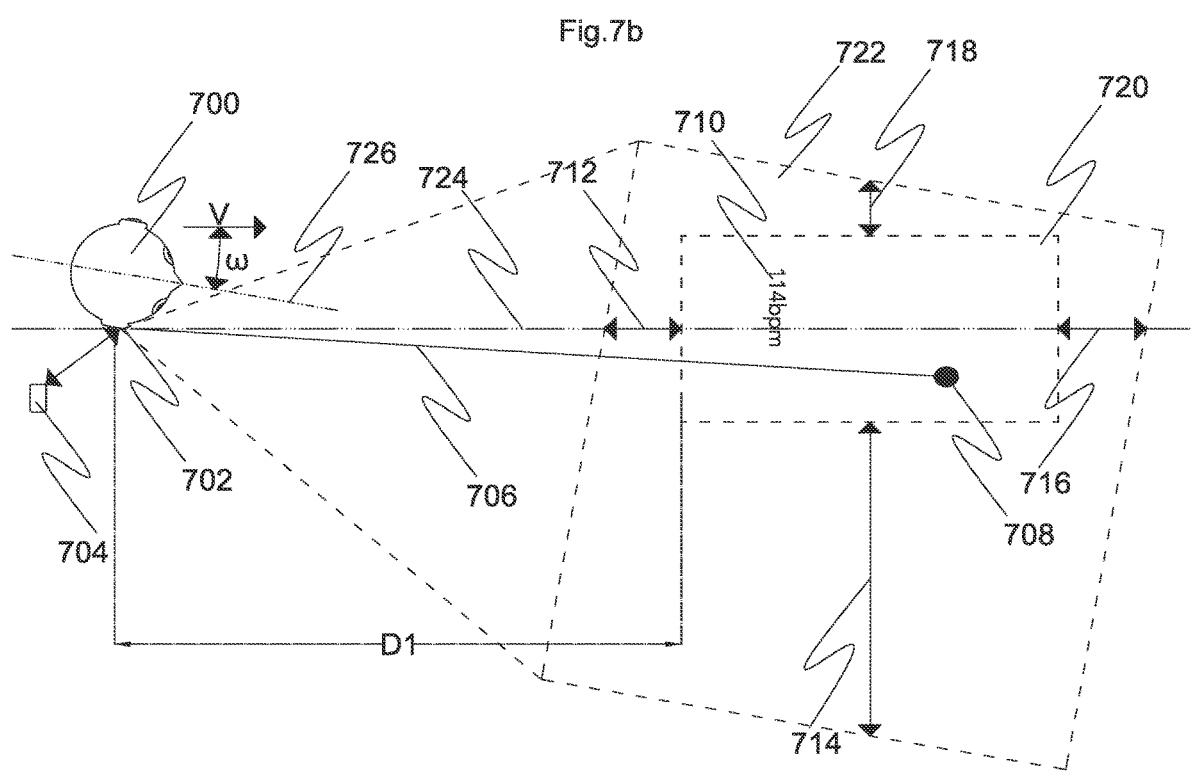

SPORTS APPARATUS FOR PROVIDING INFORMATION

CROSS REFERENCE TO RELATED APPLICATIONS

This application is a continuation-in-part application of U.S. patent application Ser. No. 15/492,372, filed on 20 Apr. 2017, the disclosure of which is incorporated herein by reference in its entirety.

FIELD

The aspects of the disclosed embodiments are directed to a device for generating a projected image, and in particular a device for converting sports activity data into an image that is projected onto a surface.

BACKGROUND

There are various devices offered for athletes to monitor bio signals (such as heart rate) and/or speed of the athlete during exercise or competition. One example of such a device is a watch having a global positioning system (GPS) sensor and means for measuring heart rate. Typically such devices have a user interface to present a parameter such as heart rate or speed to the user. A problem with visual user interfaces is that they require the user to change the pace of the training while taking a look on the user interface (of the wrist watch for example). One solution to overcome the problem is to have vibrator or similar in the device to provide alert via vibration to the user, when for example the heart rate is higher than a pre-set level or when the user runs too slow or too fast. This solution has limitations of not providing detailed information related to the training for the user.

SUMMARY

In one embodiment, a device according to the present disclosure is a device for providing information to a user, the device comprising
means for measuring speed of the device;
a sensor for detecting an orientation of the device;
a processor for creating information from the measured speed;
a light source for emitting a light beam from the device to render the information on a surface outside the device; and
at least a first actuator for adjusting a relative direction of the light beam with respect to the orientation of the device
characterised in that the information is rendered on a ground and the distance between the device and the marker is a function of the measured speed.
In one embodiment, a device according to the present disclosure is a device for generating a projected image based on an activity related parameter, the device comprising:
a first sensor for detecting the activity related parameter;
a second sensor for detecting an orientation of the device;
a processor coupled to the first sensor for creating information from the detected activity related parameter;
a light source for emitting a light beam from the device to project the created information as an image onto a surface outside the device; and
at least a first actuator for adjusting a relative direction of the light beam with respect to the detected orientation of the device,
wherein the surface outside the device is a ground surface and a distance between the device and the projected image is a function of the detected activity related parameter.
In one embodiment, a system according to the present disclosure is a system for providing information to a user, the system comprising;
means for measuring a parameter related to a movement;
means for using the measured parameters to create information;
a device for rendering the information to the user;
the device comprising
a sensor for detecting an orientation of the device;
a light source for emitting a light beam from the device to render the information on a surface outside the device; and at least a first actuator for adjusting relative direction of the light beam with respect to the orientation of the device characterised in that the information is rendered on a ground and the distance between the device and the marker is a function of the measured parameter, and the parameter is a speed of the user, measured with measurement means.
In one embodiment, a system according to the present disclosure includes a system for generating a projected image based on an activity related parameter, the system comprising;
a processor configured to determine the activity related parameter;
the processor configured to convert the determined activity related parameter into an image; and
a device for projecting the image onto a surface;
the device comprising:
a light source for emitting a light beam from the device to project the image onto the surface, the surface being outside the device; and
at least a first actuator for adjusting a relative direction of the light beam towards the surface with respect to an orientation of the device relative to the surface,
the wherein the surface is a ground surface and a distance between the device and a position of the projected image on the ground surface is a function of the determined activity related parameter.

BRIEF DESCRIPTION OF THE DRAWINGS

FIG. 7a is a schematic illustration of an exemplary implementation according to an embodiment seen from above;

FIG. 7b is a schematic illustration of an exemplary implementation according to an embodiment seen from above;

DETAILED DESCRIPTION

Figure 1A:
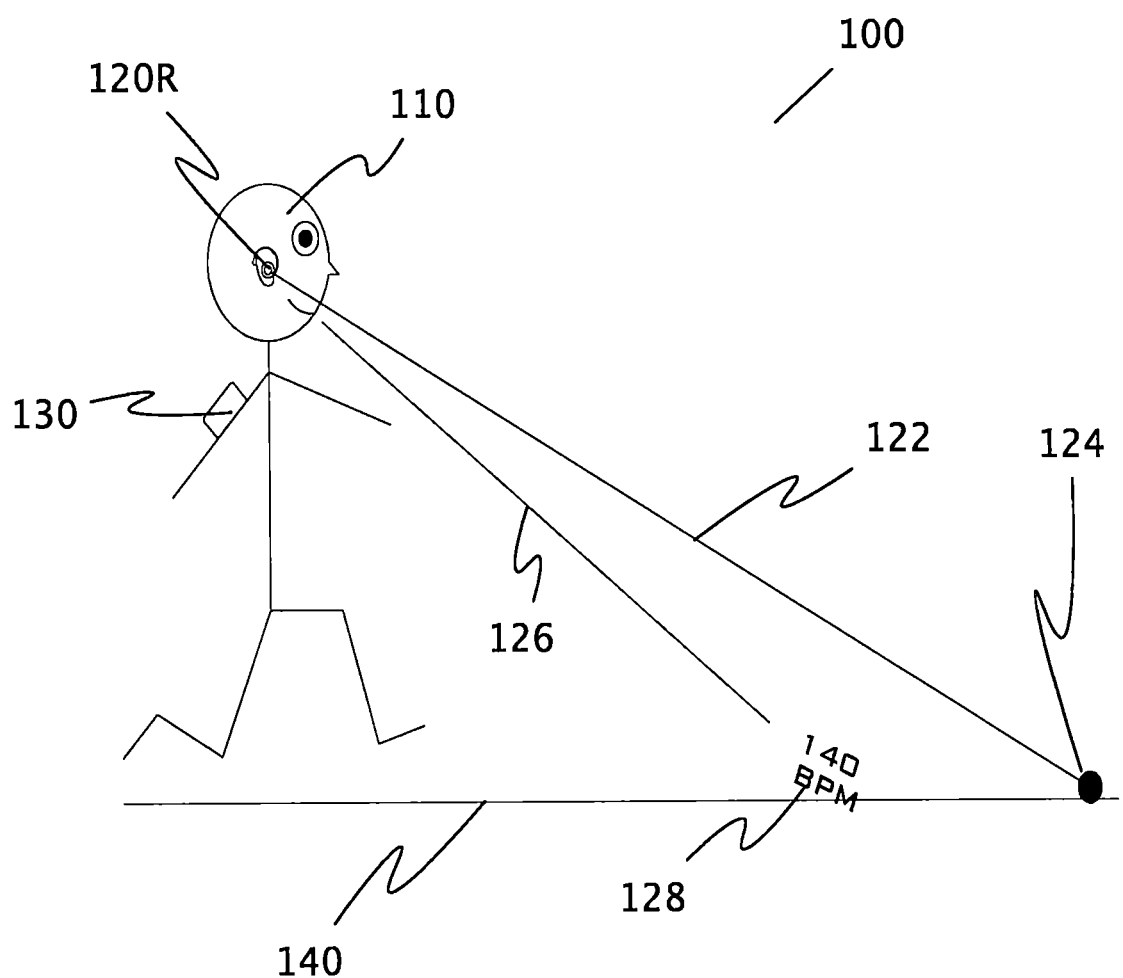
FIG. 1A is a schematic illustration of an exemplary implementation according to an embodiment seen from a side.

A device for providing information to a user, the device comprising
means for measuring speed of the device;
a sensor for detecting orientation of the device
a processor for creating information from the measured speed;
a light source for emitting a light beam from the device to render the information on a surface outside the device; and
at least a first actuator for adjusting relative direction of the light beam with respect to the orientation of the device,
wherein in that the information is rendered on a ground and the distance between the device and the rendered information is a function of the measured speed.

A device for generating a projected image based on an activity related parameter, the device comprising:
a first sensor for detecting the activity related parameter;
a second sensor for detecting an orientation of the device;
a processor coupled to the first sensor for creating information from the detected activity related parameter;
a light source for emitting a light beam from the device to project the created information as an image onto a surface outside the device; and
at least a first actuator for adjusting a relative direction of the light beam with respect to the detected orientation of the device,
wherein the surface outside the device is a ground surface and a distance between the device and the projected image is a function of the detected activity related parameter.

The device can be used to render information such as speed of the device or indication of the speed of the device, using a beam of light emitting from the device. The device has means for measuring speed of the device, such as a speedometer or navigation device. The measured speed is used to create activity related information and data using a processor. In one embodiment, the processor is, or is connected to a computer or computing device, such as a mobile computing or communication device, or example. Example information is or can be converted into a graphical illustration of a number value representing the speed. Other examples can include using colours to indicate or represent the activity related data, such as speed. For example, in one embodiment, a red dot can be used to indicate that the detected speed is too high compared to a target speed.

The device has a light source for emitting a light beam from the device to render or otherwise project the information onto a surface outside of the device. In one embodiment, the surface outside of the device is the ground or other such surface. Rendering of the information refers to illuminating or projecting a light image onto a surface such as the ground with the beam or beams of light.

In one embodiment, the device has a sensor to detect an orientation of the device. The orientation information is used to determine where to direct the beam of light from the device with respect to the orientation of the device. The direction of the light that is projected from the device can be adjusted with one or more actuators that control the position of the light source in the device.

The device has the advantage that it solves the problem of needing to change pace of training to take a look on a user interface, such as a watch or similar device. The device of the disclosed embodiments also enables giving detailed information related to training for the user. The information is rendered on a ground at a distance from the device. The distance between the device and the rendered information is a function of the measured speed. In one embodiment, the rendered information can be projected relative to a baseline marker that allows the user to view how close or far the user is from a baseline parameter, such as a predefined or target pace or heart rate.

In an example embodiment the device is attached to a bicycle using for example a bracket or other attachment mechanism. In one embodiment, the bracket is a quick release mechanism and can include a gripping or quick lock device that can be secured in place as well as released. The attachment device could also include a releasable mechanism such as Velcro. The aspects of the disclosed embodiments are not intended to be limited by manner in which the device is attached or coupled to the user, which in this example is via the bicycle. Although a bicycle is referred to herein, the aspects of the disclosed embodiments are not so limited and can include any suitable type of transportation mode or vehicle that is used for sports.

The information is projected on the ground in front of the bicycle. The device enables more safe cycling since the speed reading can be rendered further away from the bicycle when the speed is high compared to when the speed is low. This way user can concentrate on traffic and other obstacles better than if the speed was only displayed in a display screen attached in the bike body or users wrist. The aspects of the disclosed embodiments allow the user to keep looking forward. This is unlike the devices of the prior art, such as a watch, which require the user to shift the attention and divert the eyes toward the watch or other such device to see the measured speed or heart rate.

In an alternative embodiment a device according to the present disclosure is a device for providing information to a user, the device comprising
means for measuring heart rate of the user;
a sensor for detecting orientation of the device;
a processor for creating information from the measured heart rate;
a light source for emitting a light beam from the device to render the information on a surface outside the device; and
at least a first actuator for adjusting relative direction of the light beam with respect to the orientation of the device,
wherein the information is rendered in the form of a marker on a ground and the distance between the device and the marker is a function of the measured heart rate.

The device can be used to render information such as heart rate of the user or indication of the heart rate of the user for the user, using a beam of light emitting from the device. The device can render a speed of the device. Rendering of the information refers to illuminating a surface such as the ground with the beam of light. The device has a sensor to detect orientation of the device when the device is used by the user. The orientation information is used to determine where to direct the beam of light from the device with respect to the orientation of the device.

The direction of the light can be adjusted with one or more actuators. The device has the advantage that it solves the problem of needing to change pace of training to take a look on user interface in a watch or similar. The device also enables giving detailed information related to training for the user. According to an embodiment, the means for measuring the heart rate is a photo plethysmography sensor (PPG).

According to an embodiment, the sensor that is used to determine an orientation of the device can include an accelerometer or a gyroscope. The accelerometer can be a 3-way accelerometer for detecting orientation of the device with respect to X, Y and Z axis.

According to embodiment means for determining or detecting the speed of the device, generally referred to herein as measuring, can be a satellite navigation sensor (such as global positioning system (GPS)) or a speedometer. In alternate embodiments, the device for determining or detecting speed can include any suitable sensors or speed measurement device other than including GPS or a speedometer. For example, in one embodiment, the speed detecting device can include an air speed sensor.

According to an embodiment, the first actuator is arranged to rotate at least one part of the device to change direction of the light beam. The rotation of the one part of the device changes the direction of the light beam. Further, the rotation of the at least one part of the device might be done in order to stabilize the device or to provide rough direction to the light beam. Further, the rotation can be used to compensate for the up and down movement of the device when attached to a target vehicle. Further, the rotation can be used to compensate tilting of the device when attached to the target vehicle. The rotation can be used to keep the overall orientation of the light source in a pre-determined angle in relation to the ground (i.e. a horizontal plane). Alternatively, the first actuator can move a first mirror, the first mirror arranged in a path of the light beam, to change direction of the light beam.

According to an embodiment, the device further comprises
 a second mirror arranged in a path of the light beam, and
 a second actuator connected to the second mirror and arranged to rotate the second mirror to change direction of the light beam.

The second actuator can be used to rotate one or more mirrors other than including the second mirror to adjust direction of the beam of light. The second actuator can be used to change orientation of a mirror to which the light beam is directed, to change direction of the light beam. The second actuator can also be used to render text and/or graphics.

According to an embodiment, the light beam is a laser light.

According to an embodiment the device comprises attachment means for attaching the device in or onto the target vehicle. The target vehicle can be according to an embodiment a bicycle. The device can be attached for example on a handle bar or other suitable part of the frame of the bicycle. In one embodiment, the device can be attached to or be part of a helmet or other suitable headgear of a user riding the bicycle. In one embodiment, the device is configured to be attached to or part of eye protection or eye glasses the user may wear, such as sport glasses.

According to an embodiment, the information is rendered in the form of a marker on a ground and the distance between the device and the marker is a function of the measured speed. In other words the device can use speed information to determine a distance from the device where the marker should be rendered. Further the marker can be a rendering which indicates a speed of the device (and thus speed of the target vehicle it is attached to). For example, in one embodiment, the marker is an alphanumeric image that indicates the speed of the device, or the other information as is generally described herein.

Further, the device can comprise means for measuring a heart rate of the user (or it can comprise means for receiving a heart rate of the user). The device can use a heart rate of the user (i.e. device) to determine where the marker should be rendered. Further the marker can be a rendering which indicates a heart rate of the user. Alternatively the information is rendered as form of marker as function of the speed of the device. As an example marker can be rendered on the ground as function of the device speed. In one embodiment, a heart rate sensor can be used to detect the heart rate of the user and to communicate the heart rate to the device. For example, a smart watch or chest strap that includes a heart rate sensor(s) can be configured to wirelessly communicate the heart rate data to the device over a suitable wireless communication protocol such as BLUETOOTH™ or ZIG-BEE™. In one embodiment, the device includes a wireless communication receiver that is configured to receive data, such as the speed or heart rate data. A processor in the device can be configured to process and otherwise convert the received data, such as the speed or heart rate data into the image data as is generally described herein.

In one embodiment, the device and marker described herein can be used as a training guide or coach. For example, in one embodiment, the marker is projected in a manner that is further away from user (or the device) when the speed is low or below a set threshold to indicate that user should speed up the training (for example cycling). As the user sees the marker far away, it is an indication for trying to catch up the marker, thus motivating to cycle faster. On the other hand, the marker could be configured to be projected on the ground closer to the user or some other predetermined marker, when the speed is higher than the determined target speed. This would indicate to the user to slow down. The marker could be set to be for example to 3-6 meters in front of the user when the speed is at the target.

An alternative embodiment is to set a heart rate for the user (for running or walking or cycling exercise). The rendered marker on the ground would be further away from the user if the heart rate is too low and close to user if the heart rate is too high. The marker could be set to be for example to 3-6 meters in front of the user when the speed is at the target. In this manner the user can readily visualize the heart rate information without any need to direct or divert the eye position away from the path in front.

The term "marker" is used herein to refer to a variety of different information, images and objects that might be projected onto a surface such as the ground using a light source or sources. Examples of such markers that may be generated by a beam of light or light source can include, but are not limited to text, numbers and/or graphics. The text could indicate for example the heart rate or the speed of the user. The rendered graphics could be at a pre-determined distance from the user all the time or the distance could vary depending on the heart rate or the speed of the user as explained above in connection with the marker.

According to an embodiment, the device comprises attachment means for attaching the device in a bicycle.

A system for providing information to a user the system comprising;
  means for measuring a parameter related to a movement;
  means for using the measured parameters to create information;
  a device for rendering the information to the user;
  the device comprising
  a light source for emitting a light beam from the device to render the information on a surface outside the device; and
  at least a first actuator for adjusting a relative direction of the light beam with respect to an orientation of the device,
  wherein the information is rendered on a ground surface and the distance between the device and the marker is a function of the measured parameter, and the parameter can include a speed of the user, measured with measurement means.

A system for generating a projected image based on an activity related parameter, the system comprising:
  a processor configured to determine the activity related parameter;
  the processor configured to convert the determined activity related parameter into an image; and
  a device for projecting the image onto a surface;
  the device comprising:
  a light source for emitting a light beam from the device to project the image onto the surface, the surface being outside the device; and
  at least a first actuator for adjusting a relative direction of the light beam towards the surface with respect to an orientation of the device relative to the surface,
  the wherein the surface is a ground surface and a distance between the device and a position of the projected image on the ground surface is a function of the determined activity related parameter.

In one aspect, the disclosed embodiments are directed to a system for providing projecting an image based on detected parameters such as sports related activity, the system comprising
  means for measuring a parameter related to the user;
  means for using the measured parameters to create information;
  a device for rendering the information to the user;
  the device comprising
  a sensor for detecting an orientation of the device;
  a light source for emitting a light beam from the device to render the information on a surface outside the device; and
  at least a first actuator for adjusting relative direction of the light beam with respect to the orientation of the device,
    wherein the information is rendered in a form of a marker on a ground and the distance between the device and the marker is a function of the measured parameter, and the parameter is one or more of
      a heart rate of the user, measured with a heart rate monitoring device,
      a speed of the user, measured with a location sensor.

According to an embodiment, the means for measuring the parameter is a portable computing device. The portable computing device can be for example a smart phone, a phone, a heart rate monitor, a global position system (GPS) device, a speedometer or similar. The portable computing device can include one or more processors coupled to memory storage device, and can be configured to execute non-transitory machine readable instructions configured to carry out the processes and methods that are generally described herein.

In one embodiment, the heart rate of the user can be measured with a heart rate monitoring device or with the device, and the speed of the user can be measured with a location sensor or speedometer. The location sensor can be for example a GPS.

According to an embodiment, the portable computing device can be configured to communicate with the device. The portable computing device can be configured to collect measurement data from the device and/or it can be configured to provide information to the device such as audio to be played with the device. Further the portable computing device can be configured to provide measurement information over a communication network to a server system.

According to an embodiment the system further comprises means for determining a velocity vector of the device. The velocity can be determined/measured with speedometer. A speedometer arrangement can be implemented for example by attaching a magnet in a wheel and magnetic reed in a body of the bicycle. Number or revolutions of the wheel per unit of time combined with information of diameter of the wheel can be used to determine the speed. Further the speed can be measured with satellite navigation system such as global positioning system (GPS). The GPS can be inside of the device. The speed information can be also obtained from a portable computing device communicating with the device. According to embodiment the velocity vector can be used to determine location of information rendering area in respect the device.

According to embodiment the system further comprises means for attaching the device to a bicycle. The attachment means can be flexible or adjustable member. The device can be releasable attached with the attachment means.

According to embodiment the rendered information is a marker and distance of the marker from the device is function of speed of the device.

DETAILED DESCRIPTION OF THE DRAWING

Figure 1B:
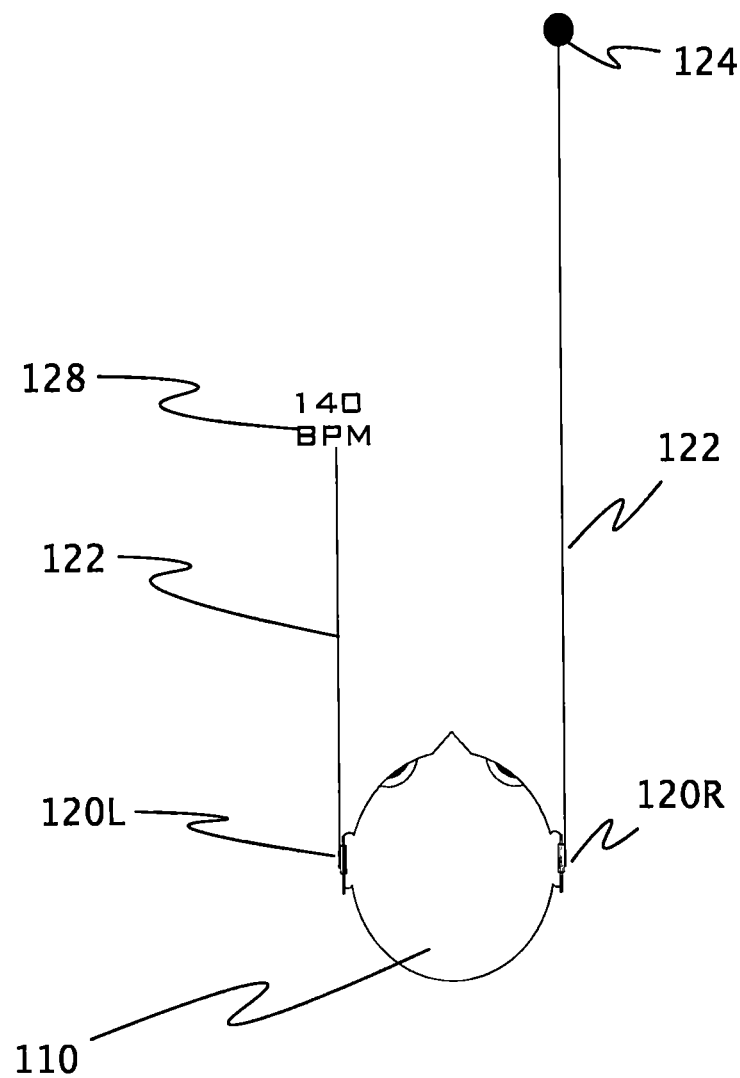
FIG. 1B is a schematic illustration of the implementation of FIG. 1A, seen from above.

FIG. 1A and FIG. 1B provide an illustration of an environment 100 according to an embodiment. A user 110 with two devices 120R and 120L attached in his ears is illustrated. The device 120L is attached to the left ear and the device 120R is attached to the right ear of the user 110. The devices 120R and 120L have a light source to render information for the user 110. The information is rendered on the ground 140.

The light beam 122 from the device 120R is used to render a dot 124 on the ground 140 and the light beam 126 from the device 120L is used to render a text and numbers on the ground 140. In the present example, text and numbers could indicate for example the heart rate of the user 110.

The user 110 has a portable computing device 130 attached to his arm. The portable computing device 130 can be used to send and receive information to/from the device 120L and/or 120R. A Bluetooth connection can be used for wireless communication. The devices 120R and 120L can be also connected with wires to the portable communication device and/or to each other. The information from the device can be for example the measured heart rate of the user. The information from the portable computing device can be for example audio. The portable computing device 130 can be used to communicate with external services and also to determine location of the user using global position system (GPS) of the portable computing device 130.

Figure 2A:
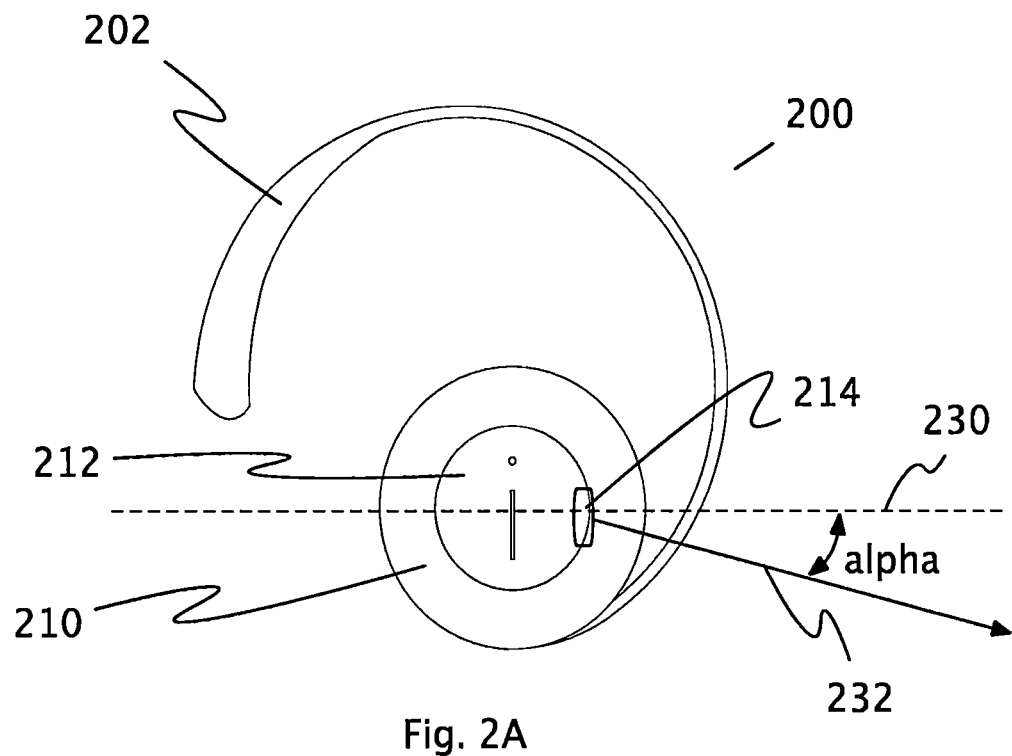
FIG. 2A is an illustration of a device according to an embodiment seen from a side.
Figure 2B:
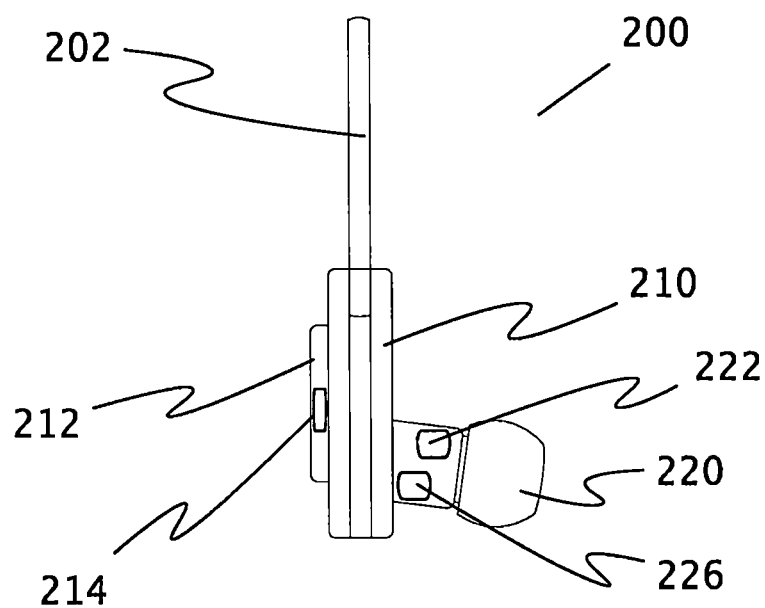
FIG. 2B is an illustration of the device of FIG. 2A seen from the front.

FIG. 2A is a side view illustration of a device 200. FIG. 2B is a front view illustration of the device 200. The device 200 has attachment means 202 to attach the device 200 to an ear of a user. The device 200 has a main body part 210 and beamer part 212. The beamer part 212 has an optically transparent opening 214 for directing light beam 232 from the device 200.

The dotted line in FIG. 2A represents a horizontal line 230 in respect to the ground. The device 200 has an orientation sensor to detect direction of the ground. The orientation sensor is an XYZ-accelerometer sensor of which readings can be used to detect the direction of the ground with respect to the device 200. The beam 232 is directed from the device 200 with angle alpha in relation to the horizontal line 230.

The device has a plug 220 which can be inserted in the ear of the user. The plug is used to provide audio from speaker 226 to the user. The plug has an infrared (IR) transmitter receiver pair 222 to detect the heart rate of the user. The IR pair 222 measures heart rate using photoplethysmogram (PPG).

Figure 3A:
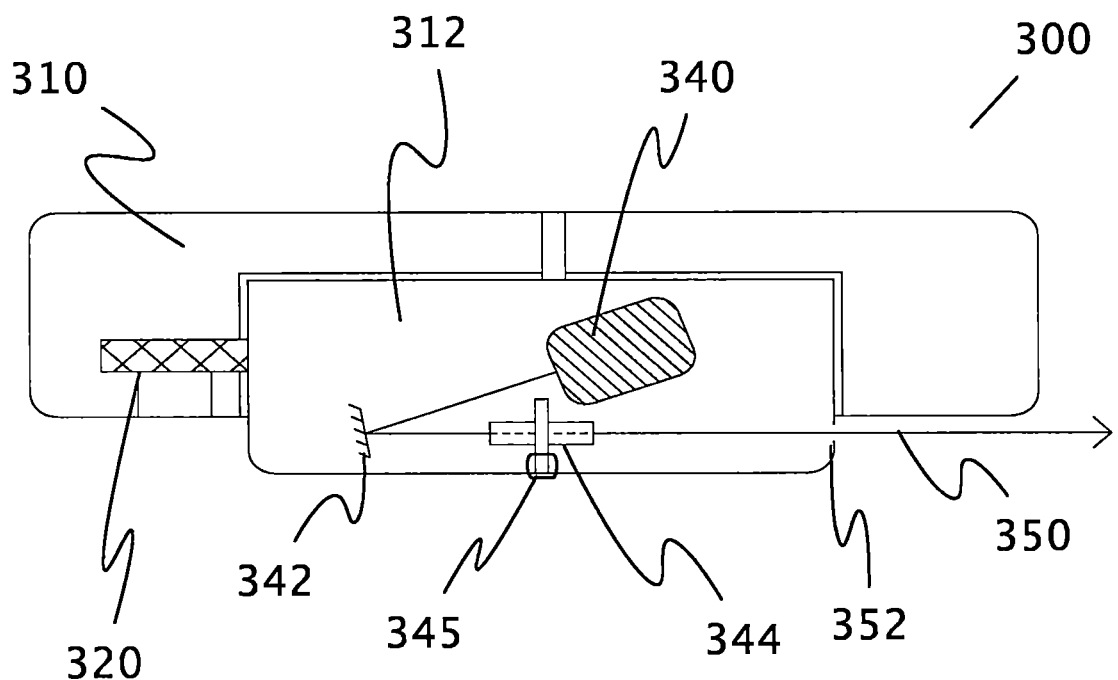
FIG. 3A is an illustration of mechanics of a device according to an embodiment seen from above.
Figure 3B:
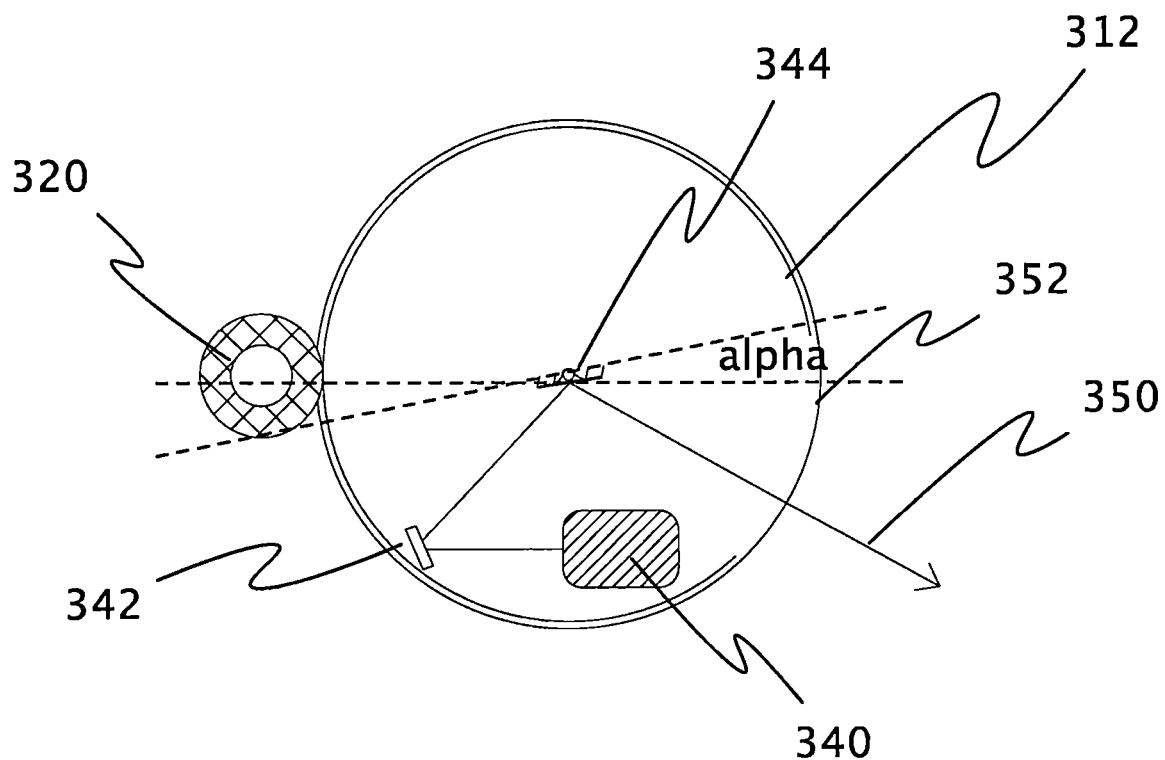
FIG. 3B is an illustration of the mechanics of the device of FIG. 3A seen from the side.

FIG. 3A is an illustration of some of the mechanics of a device 300 seen from top. FIG. 3B. is an illustration of some of the mechanics of the device 300 seen from the side.

A stabilizing actuator 320 is connected to a body part 310. The stabilizing actuator 320 is used to rotate the beamer part 312. The rotation causes a change in the angle between a horizontal line and a beam 350. This is used to a) direct the light to an appropriate distance from the user and b) to keep the direction of light with respect to a horizontal line substantially constant to compensate head movements. A rotation angle is controlled by a microcontroller in the device 300.

A light beam 350 is generated by a light source 340. In one embodiment, the light beam 350 from the light source is reflected from one or more of a first mirror 342 to a second mirror 344. The beam of light 350 goes through an optically transparent opening 352. The first and second mirrors 342 and 344 are actuated with a first actuator and a second actuator 345. The first and second actuators are used to control direction of the light beam 350 to render text, numbers and/or images on the ground at an appropriate distance (as adjusted with the stabilizing actuator). In one embodiment the first mirror 342 is attached to the beamer part and the second mirror 344 is actuated by a second mirror actuator 345 (with a motor or servo). The first actuator can thus be the same that is used for adjusting the relative direction of the light beam, or it can be a separate, mirror actuator.

Alternatively, the stabilizing actuator 320 is used to keep the beamer part 312 at a pre-determined orientation with respect to the ground and the mirror actuators are used to control distance of graphics or dots from the user.

The device 300 can be used to provide a simple indication to the user. As an example, a dot of light is rendered on the ground at distance from the user. The distance between the dot of light and the user is longer when the heart rate is low. The distance between the dot of light and the user is shorter when the heart rate is high. This enables an intuitive way for the user to adjust his/her pace of running or walking or cycling. A target is to get the dot to say at a predetermined distance from the user, not too far (too low heart beat thus not exercising sufficiently) and not too close (too high heart beat). In an embodiment, the distance of the dot from the user is controlled by rotating the beamer part 312 with the stabilizing actuator 320. In case of rendering text or other graphics on the ground, the rotation is used to define a centre area for the rendered text or graphics and the mirror actuators are used to draw the graphics in proximity of the centre area.

Further, in FIG. 3B dashed lines are drawn to illustrate an angle alpha between a horizontal line going through a mid-point of the beamer part 312 and a stabilizing actuator 320 and a mirror 344.

Figure 4:
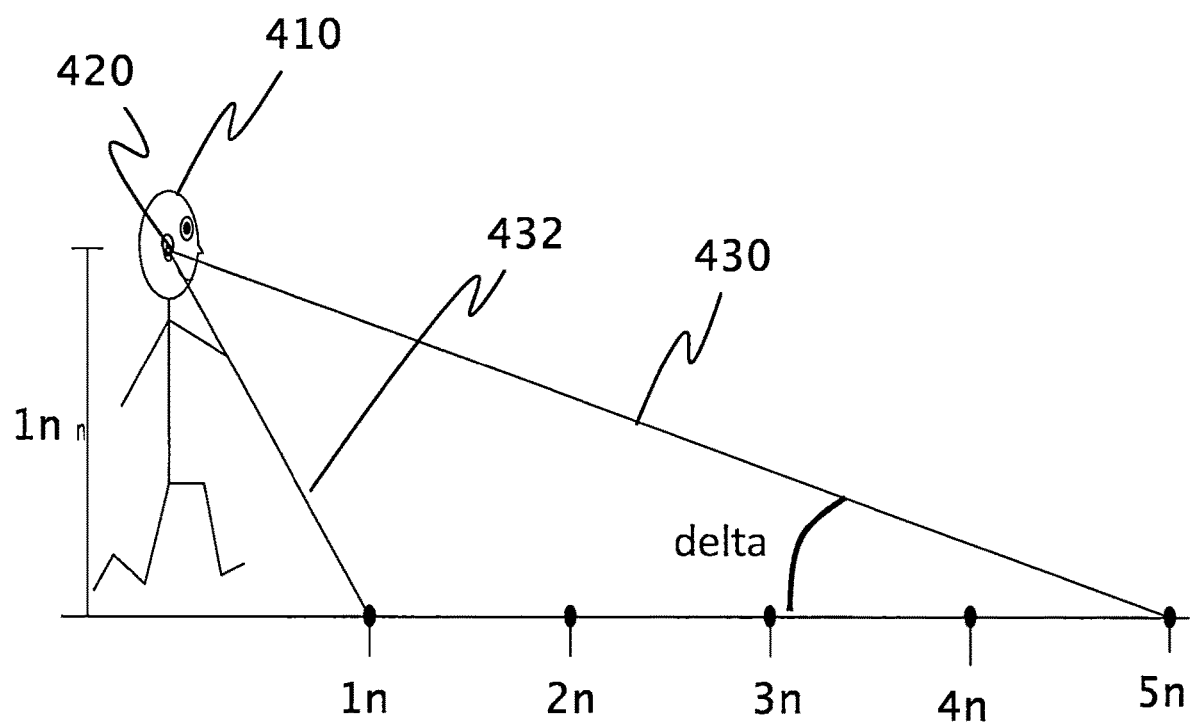
FIG. 4 is a schematic illustration of a setup according to an embodiment seen from a side.

FIG. 4 is an illustration of how the distance of the light dot created by a beam of light 430, 432 on the ground from the user 410 can be adjusted. The user has the device 420 attached to his/her ear at a height 1n from the ground. The light beam 430 creates a dot at a distance 5n and a light beam 432 at distance 1n.

Based on an embodiment, either the stabilizing actuator or the second mirror is used to adjust the distance of the dot from the user by adjusting the angle of light emitting from the device 420 with respect to the device 420. Based on an embodiment, the distance of the dot from the user is a function of the heart rate. If the heart rate is in the desired range the dot is illuminated at a distance between 2n and 3n. If the heart rate is higher than the desired rate, the dot is illuminated at a distance between 1n and 2n. If the heart rate is lower than desired rate, the dot is illuminated at a distance greater than 3n.

Figure 5A:
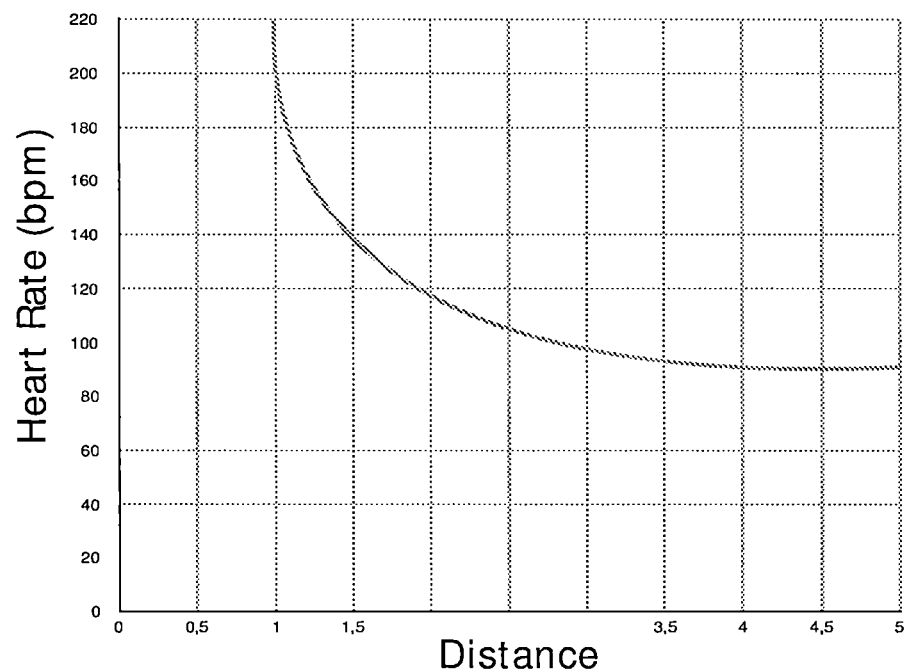
FIG. 5A is an example of correlation between distance for rendering the information and heart rate according to the disclosed embodiments.
Figure 5B:
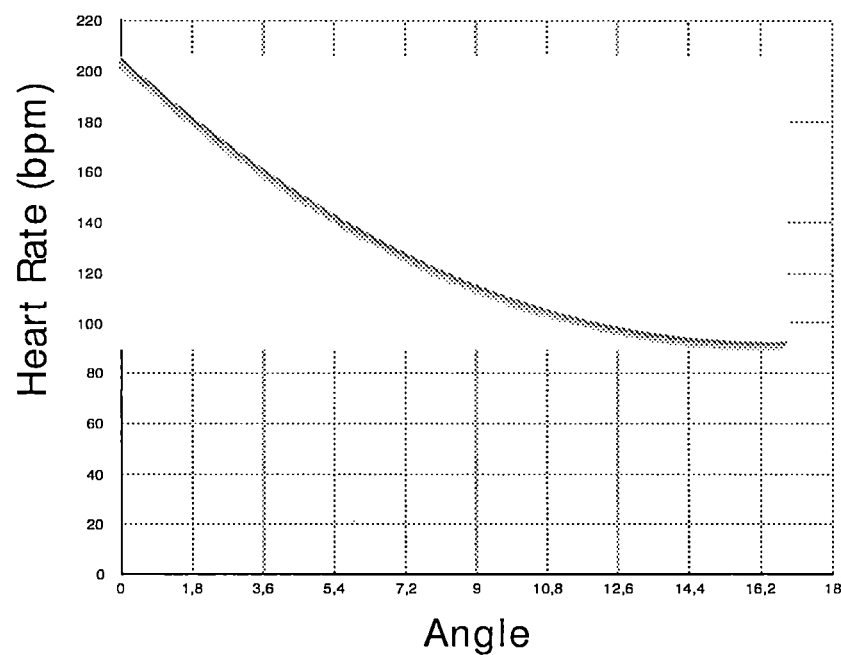
FIG. 5B is an example of correlation between the angle of light from the device with respect to the ground and heart rate according to the disclosed embodiments.

FIG. 5A shows an example correlation curve between the distance of the dot and the heart rate. FIG. 5B shows an example of the angle of the actuator mirror with respect to the horizontal line for the respective heart rate.

One way to calculate the angle between a second mirror 344 and the horizontal line is using equation $$\alpha = 22.5° - 0.5\delta$$

wherein delta is a desired angle between the ground and the beam.

Figure 6:
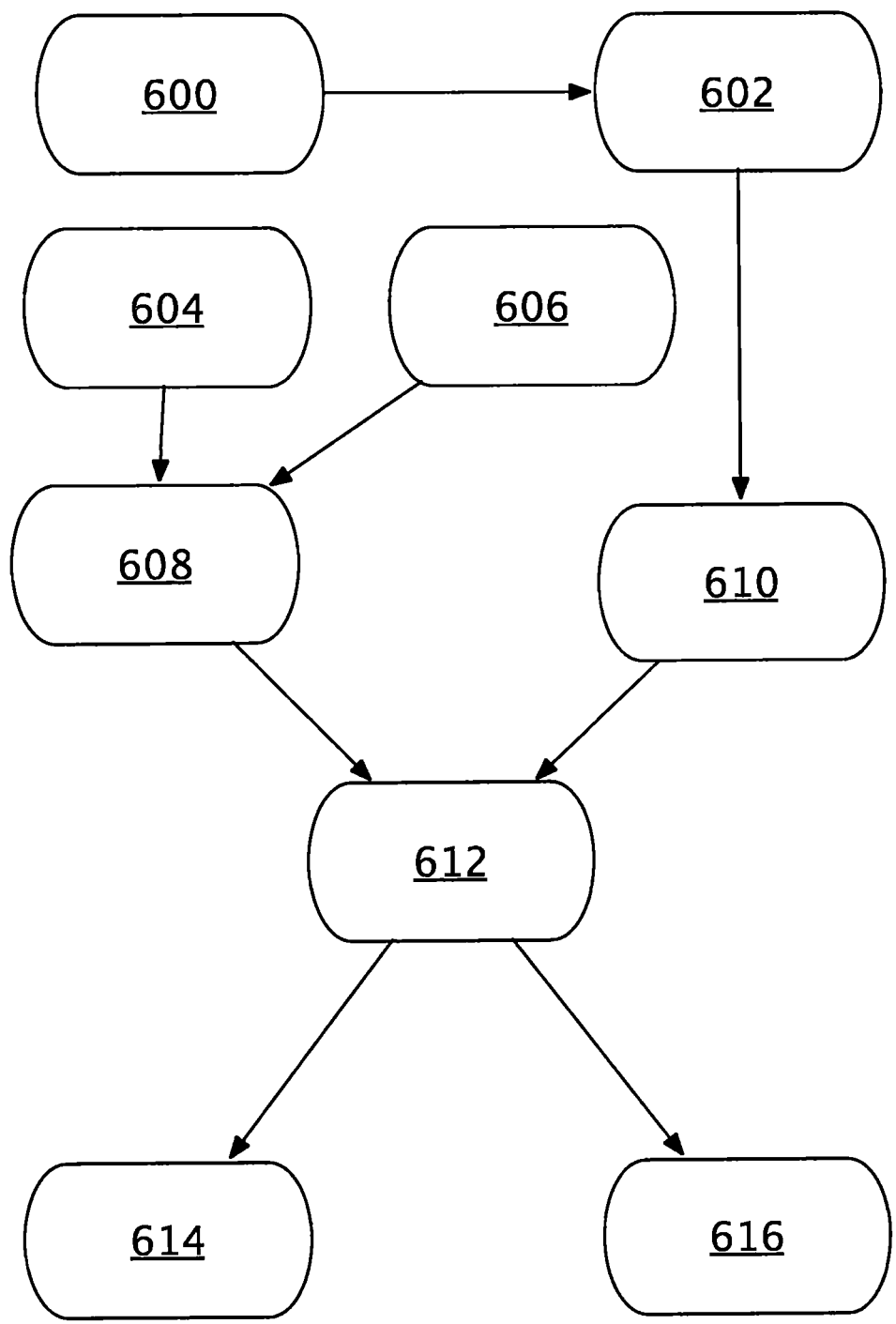
FIG. 6 is a schematic illustration of some functional modules of the device incorporating aspects of the disclosed embodiments.

FIG. 6. is an illustration of modules related to the device and some information flows between the modules. A heart rate monitor module 600 provides heart rate related data or information such as beat-to-beat frequency to a heart rate data analyser module 602. The analysed data is used to make control parameters related to directing light from the device in a heart rate function module 610. A module as is generally comprised herein can comprise or include one or more of a processor or a computing device that includes a processor. A module can be configured to execute non-transitory machine readable instructions to carry out the functions and processes generally described herein.

An orientation sensor module 604 (such as gyroscope or accelerometer) provides orientation information with relation to the ground. The information from the sensor module 604 is processed with an algorithm from an accelerator processing module 606.

Information from the orientation sensor module 604 is analysed in a movement and orientation analyser module 608 using an algorithm and parameters from the accelerator processing module 606 to determine possible periodic or semi-periodic movements of the user as well as the angle of the device with respect to the ground.

As an example, movements can be predicted with a function taking in consideration running/walking habits of the user. Acceleration of the device can be estimated as function of time, t as:

$$a(t) = \frac{h}{2}\left(\frac{\pi v}{s}\right)^2 \cos\left(\frac{\pi v}{s}t\right)$$

where h is a vertical distance change of the device, when it moves with the head when in use (in practice ear height variation from the ground), v is speed of the user and s is a length of the step. This enables prediction of when and how to tilt mirrors or activate stabilizing actions. In practice maximum acceleration is when a feet hits ground. Accelerations of 5-8 m/s^2 were observed when testing the system.

Information from the movement and orientaion analyser module 608 and information from the heart rate function module 610 are received with a central processing unit (CPU) module 612. The CPU module 612 provides control signals for stabilizing the actuator motor controlling module 614 to rotate the beamer part of the device. The CPU module 612 provides control signals to the control actuators controlling module 616 moving the first and/or second mirror.

FIG. 7a is an illustration according to an embodiment of present disclosure. A user 700 (seen from top) has a device 702 attached to his head. The device 702 is connected over radio interface to a portable computing device 704. Direction of the head is indicated with line 726. The device is configured to render information within a total rendering area 722 in a ground. Information is rendered in an information rendering area 720 of the total rendering area 722.

The device 700 and/or portable computing device 704 is configured to determine velocity vector V of the user 700. The velocity vector V indicates speed and direction of the speed (in X, Y and Z components). The velocity vector V is determined by measuring velocity and direction of velocity using sensors of the device 702 and/or the portable computing device 704. Example sensors which can be used are an accelerometer or a GPS. The velocity vector can be instantaneous velocity or it can be average of velocities over time. The device 700 and/or portable computing device 704 is configured to calculate for example using Kaman filters (or moving averages) velocity vector V to eliminate random movements and rapid head movements. Alternatively direction of the velocity vector can be determined by environment where the exercise is taken place. For example if runner is in standard 400 m oval track the velocity vector can be turned automatically to follow the track of where the user is running. As another example a map can be used to determine if the velocity vector direction has to be changed.

Velocity vector V is used to determine a relative location of the information rendering area 720 in respect to user 700 when the user 700 is using the device 702. The information rendering area 720 is in parallel to the velocity vector V. Line 724 illustrates direction of vector V as well as centre line of the information rendering area 720.

A laser beam 706 is used to render a marker 708 and/or parameter info 710 such as text and numbers (heart beat for example) on the ground. The information is rendered in the information rendering area 720. The information rendering area 720 is distance 718 from left side of the total information rendering area 722, distance 714 from right side of the total information rendering area 722, distance 712 from the front and distance 716 from the rear of the total rendering area 722.

The information rendering area 720 is at distance D1 from the user. Information placement within the information rendering area is varied depending on the measured parameter. For example the marker can be farther from user 700 if the heart beat is low (or speed is slow) and closer to user 700 if the heart beat is high (or speed is high).

FIG. 7B is an illustration of a situation where the head of the user 700 has turned at an angle of ω in respect to velocity vector V and the direction of the head. Since the velocity vector V has not changed (user is running in same direction) the information rendering area 720 stays in relation to user 700 in the same relative position i.e. at distance D1 in a direction of the velocity vector V. Since the head has turned the angle ω the total information rendering area has moved as indicated in the figure. The information is thus rendered in direction of velocity vector V.

Example: Uphill Running (FIG. 7C)

Figure 7C:
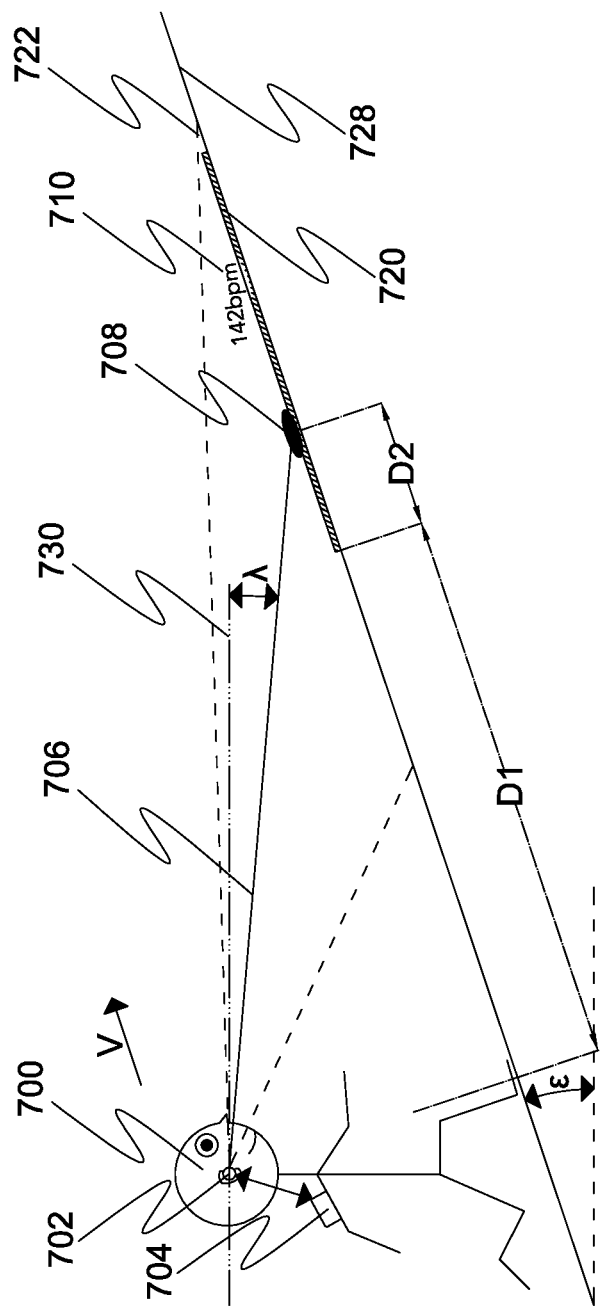
FIG. 7c is a schematic illustration of an exemplary implementation according to an embodiment seen from a side.

FIG. 7C is an illustration of a user 700 running uphill on a slope having an angle ε in respect to horizontal. The total information rendering area 722 is indicated with dashed lines. The information rendering area 720 is illustrated and it is at distance D1 from the user 700. A marker 708 is rendered with a beam of laser 706 originating from the device 702 in the ground 728. The marker 708 is rendered at distance D2 from the edge of the information rendering area 720 i.e at distance D1+D2 from the user 700. Additional information such as a heart beat 710 can be also rendered with the laser light 706. The device 702 can have an orientation sensor to detect orientation of the device 702 in respect to the horizontal. Horizontal line in respect to device 702 is indicated with a line 730.

When using the system a physiological parameter such as heart beat or velocity is determined using a sensor in or coupled to the device 702, in or coupled to the portable computing device 704 or other device such as a pulse meter. The parameter determines a distance (D1+D2) from user 700 where the marker 708 is rendered. Distance D1 is user settable value such as 1 meter. The distance D2 can be determined for example by equation:

$$D2 = \frac{HR}{55\frac{1}{\min \cdot m}}$$

wherein HR is a hearth rate (beats per minute). Value 55 is a user selectable parameter. If the heart beat is 220 beats per minute the equation will give D2 as 4 meters (i.e the marker is at distance of 1 m+4 m=5 m). If the heart beat is 110 the D2 is 2 meters (i.e the marker is at distance of 1 m+2 m=3 m).

Velocity vector V is determined by measuring direction of movement and velocity using accelerometer and/or GPS information. The velocity vector V has angle ε in respect to the horizontal.

Angle λ between horizontal line 730 and the laser beam 706 for rendering marker at distance D1+D2 from the user can be determined for example by equation:

$$\lambda = \arctan\left(\frac{h}{D1+D2}\right) - \varepsilon$$

wherein h is height of the device 702 from the ground i.e for example 160 cm if ear of the user 700 is 160 cm from the ground.

This way the marker can be rendered at the distance D1+D2 from the device independently if user is running on flat surface (ε=0) or uphill ε>0 or downhill ε<0). Needed values for the calculation are the direction of the velocity vector V and height of the device in respect to ground when in use.

Figure 8:
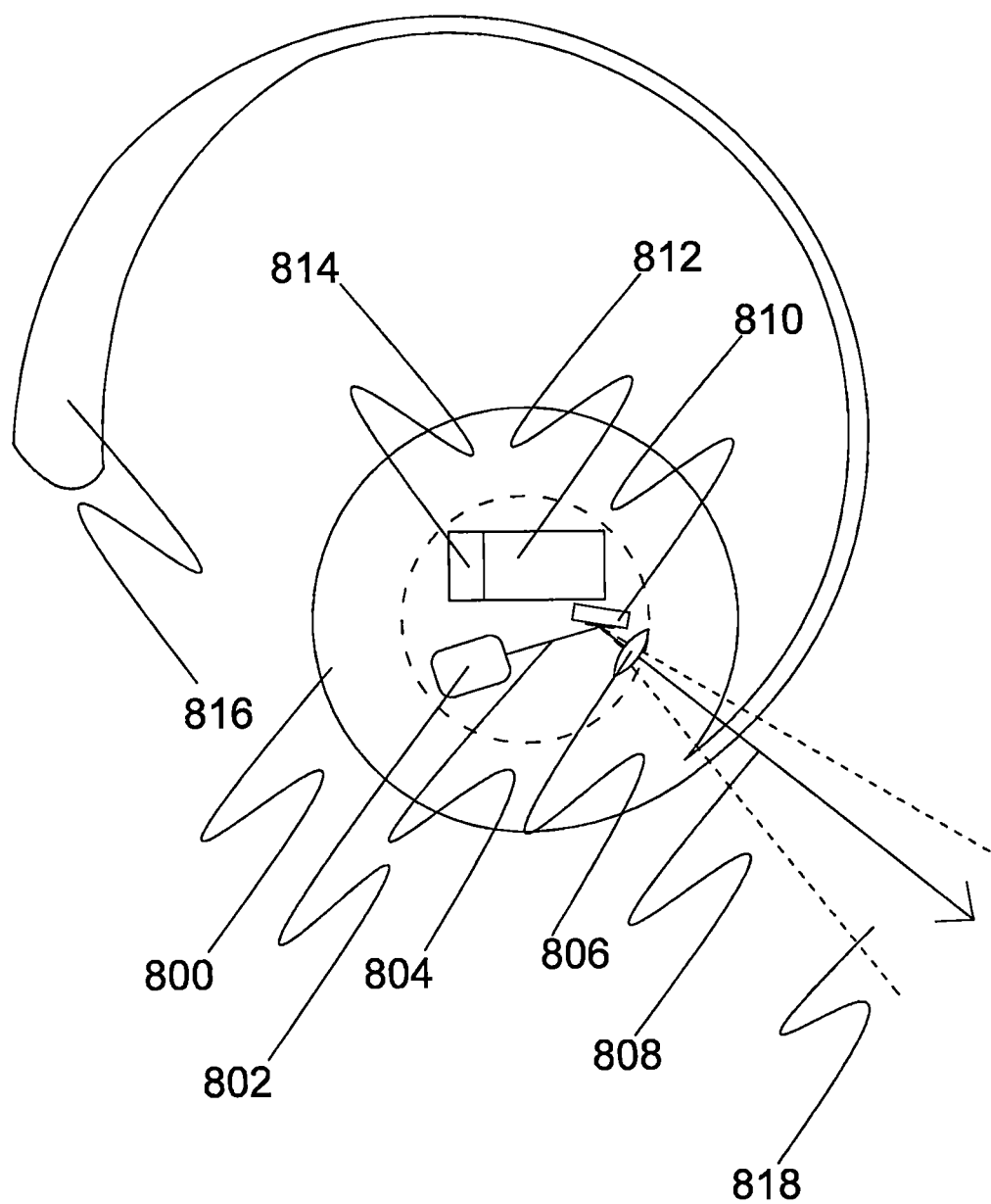
FIG. 8 is a schematic illustration of the mechanics of the device according to an embodiment.

FIG. 8 is an illustration of alternative embodiment of the device 800. A laser source 802 emits a light beam 808 via a first actuator (microelectromechanical systems (MEMS) mirror) 810 and a lens system 806. The first actuator (MEMS mirror) 810 is controlled by central processing unit (CPU) 812 to render information with the laser light 808 in an information rendering area 818. The device 800 comprises one or more sensors 814 for detecting one or more of an orientation, speed, velocity and acceleration of the device 800. The sensor information is processed in the CPU 812 to determine a velocity vector and orientation to determine area for rendering the information. The device 800 can have a radio interface such as Bluetooth™ to connect to external device such as a smart phone or biosensor (such as heart rate measurement sensor) to receive parameters related to the user and the associated activity (heart rate or velocity). The device 800 is connected to ear with attachment means 816, such as an ear clip or over the ear loop. A battery can be embedded in the attachment means. CPU uses the parameters to determine content and a relative distance of the content from the device to be rendered.

Figure 9A:
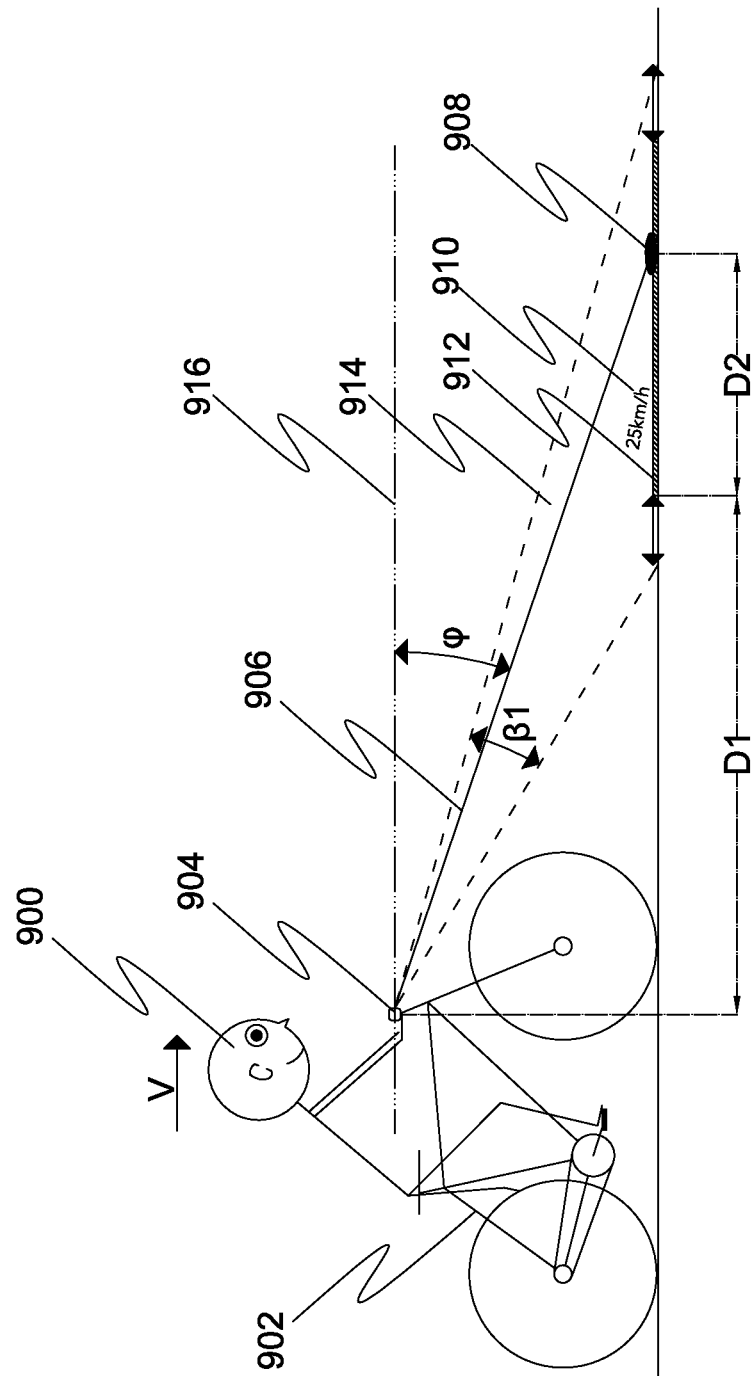
FIGS. 9A and 9B are a schematic illustration of a device incorporating aspects of the disclosed embodiments when in use in a bicycling related activity.
Figure 9B:
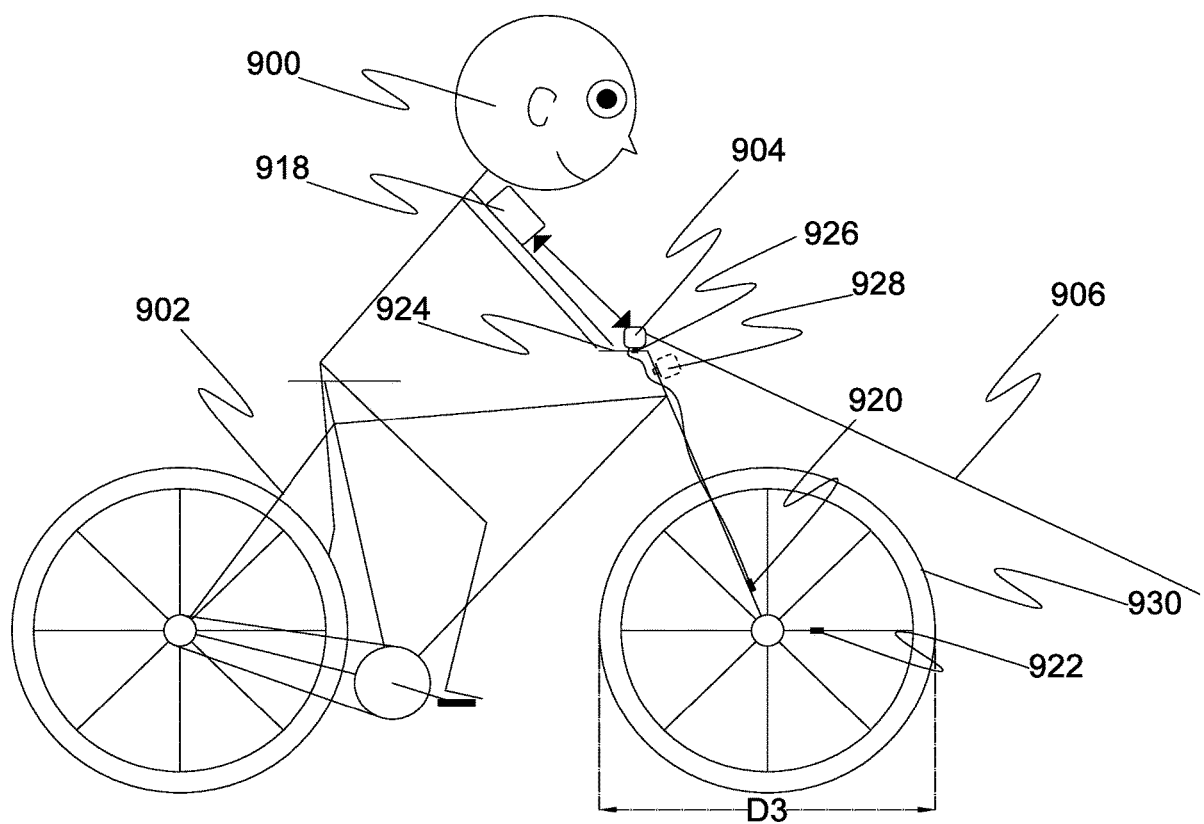

FIG. 9A and FIG. 9B are illustrations of a system where a device 904 is used with a bicycle 902 according to one embodiment. A user 900 is cycling with the bicycle 902 with velocity V to a direction indicated with an arrow. The device 904 is attached to the bicycle 902 with an attachment means. The device 904 renders information or projects and image comprising the information onto the ground in front of the bicycle 902. The rendered information or projected image (formed by one or more light beams) can be for example a maker 908 or text/numbers 910.

In one embodiment, the information is rendered with a laser beam 906 emitting from the device 904 in an information rendering area 912. A horizontal line 916 is indicated with dashed line. The horizontal line is in the direction of the velocity vector V. The device 904 can emit laser light within a total information rendering area 914 i.e. the area which can be covered with swipe angle 131. In present example the device 940 is configured to render information within the total information rendering area 914 in the information rendering area 912. The information rendering area is at distance D1 from the bicycle 902. Marker is rendered at distance D2 from the edge of the information rendering area 912. As said the marker is be configured to be further away from the device 904 when the speed is lower and closer to the device 904 when the speed is higher.

Referring to FIG. 9B the user 900 has a portable computing device 918. The portable computing device 918 is configured to communicate with the device 904 for example using low power Bluetooth™ connection. The portable computing device can be a smart phone, or for example, a device configured to measure a heart beat of the user 900. The device 904 can be connected to various parts of the bicycle for example in a handlebar 924 or for example to body 928 (the device 904 is indicated with dashed line) with an attachment mean 926. The device emits laser light 906 as described earlier. Speed of the bicycle 902 can be measured by attaching a magnet 922 in a wheel 930 and a magnetic reed 920 to record how many times per minute the wheel 930 revolves. The speed can be calculated if the diameter D3 of the wheel 930 is known. Alternative ways to determine the speed is to have a global positioning system in the device 904 or in the portable computing device 918.

Figure 10:
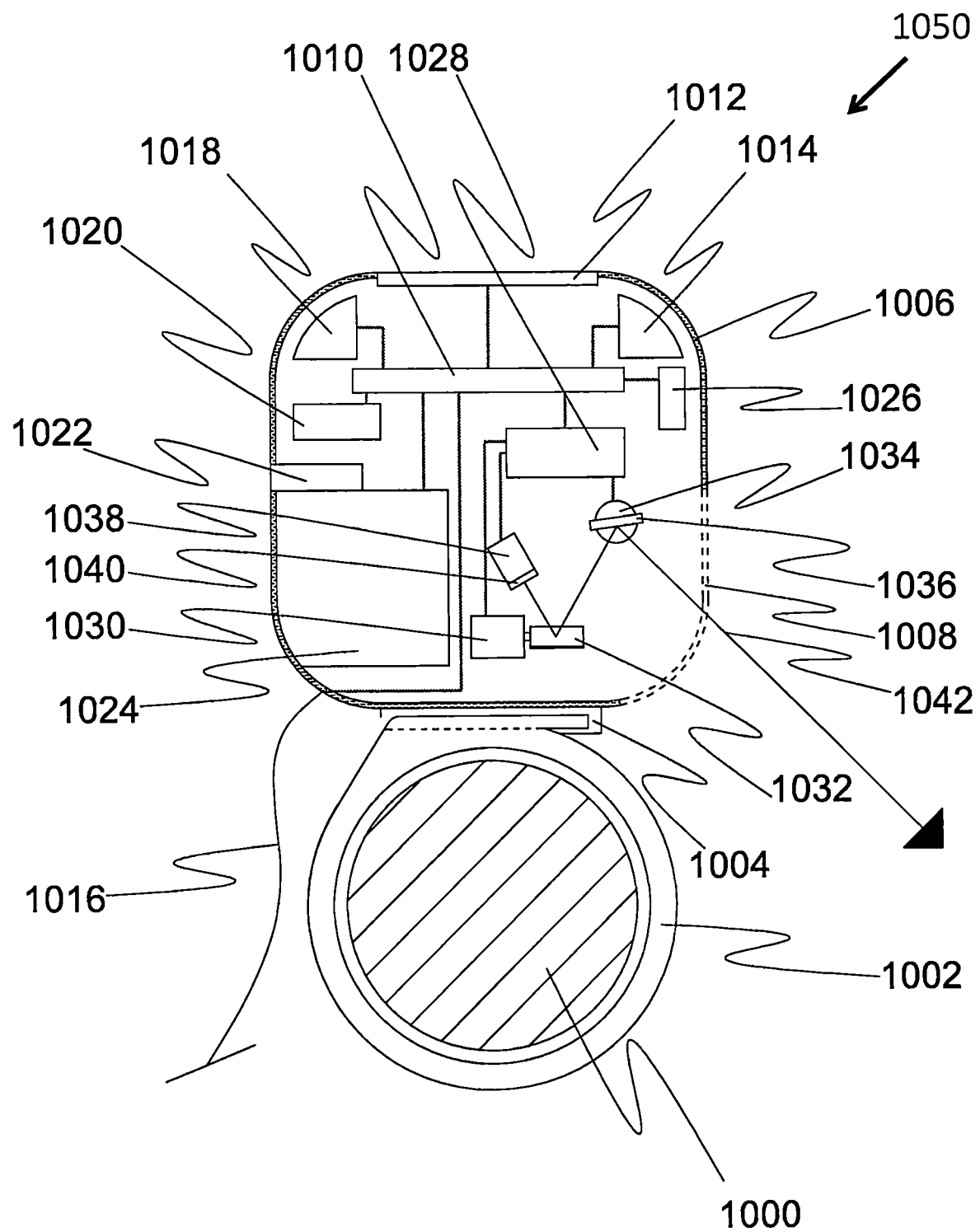
FIG. 10 is a schematic illustration of a device and its components incorporating aspects of the disclosed embodiments.

FIG. 10 is an illustration of a cross section of a device 1050 according to one embodiment. A body 1006 covers components of the device 1060. The body has a transparent opening 1008. The opening 1008 can be for example transparent plastic material forming a window to allow laser beam 1042 to emit from the device 1050. The device 1050 is attached to a handlebar 1000 with attachment means. The attachment means comprises adjustable (optionally flexible) member 1002 with protrusion. The device 1050 has a counterpart 1004 which attaches to the protrusion of the member 1002. The device 1050 can be conventionally attached and released from the attachment means. The device 1050 receives on/off signal via wire 1016 from a magnetic reed (to measure speed). The device 1050 comprises a processor 1010. The processor 1010 is configured to execute a software program stored in a memory 1026. The software program comprises non-transitory machine readable instructions related to rendering information based on input. The processor 1010 is communicatively connected to satellite navigation module 1014 (such as global position system GPS) and to communication module 1018.

The device comprises sensor 1020. The sensor 1020 can be one or more of accelerometer, gyroscope, compass, and movement sensor. The sensor 1020 is configured to detect orientation of the device 1050. The orientation of the device 1050 can be detected/measured in stationary situation and also when the device 1050 is moving. The sensor 1020 is configured to communicate sensor information to the processor 1010.

The device has user interface 1012. The user interface can be touch panel, rotatable disk, one or more buttons etc. The user interface 1012 might comprise also a display and one or more status light emitting diodes (LED's).

The device 1050 receives power from a battery 1024. The battery 1024 can be charged with a charger 1022. The charger can be universal serial bus (USB) or other charging such as inductive charging.

Rendering control unit 1028 receives rendering instructions from the processor 1010. The rendering control unit 1028 is configured to turn laser 1038 on/off. Laser beam 1042 emitting from the laser 1038 can be collimated with a lens system 1040. The rendering control unit 1028 is configured to control a second actuator 1030 to turn a second mirror 1032 to along a second axis. The rendering control unit 1028 is configured to control a first actuator 1034 to turn a first mirror 1036 to along a first axis. According to embodiment the first axis is perpendicular in respect to the second axis. Further the first and second actuators and the first and second mirrors can be according to alternative embodiment replaced with other optical arrangement such as micro electro mechanical system (MEMS) mirrors.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A device for generating a projected image based on an activity related parameter, the device comprising:
   a first sensor for detecting the activity related parameter;
   a second sensor for detecting an orientation of the device;
   a processor coupled to the first sensor for creating information from the detected activity related parameter;
   a light source for emitting a light beam from the device to project the created information as an image onto a ground surface outside the device; and at least a first actuator for adjusting a relative direction of the light beam with respect to the detected orientation of the device, wherein a distance between the device and the projected image is a function of the detected activity related parameter, wherein the projected image is a marker of light rendered on the ground surface at a distance from the device, which marker of light is rendered on the ground surface further away from the device if the activity related parameter is low and closer to the device if the activity related parameter is high.

2. The device according to claim 1, wherein the second sensor is an accelerometer or a gyroscope.

3. The device according to claim 1, wherein the first sensor is a speed measurement device and comprises a satellite navigation sensor or a speedometer.

4. The device according to claim 1, wherein the first actuator is configured to rotate a first mirror arranged in a path of the light beam to change a direction of the light beam.

5. The device according claim 4, further comprising:
a second mirror arranged in the path of the light beam; and
a second actuator connected to the second mirror and configured to rotate the second mirror, to change the direction of the light beam in a direction that is perpendicular with respect to the first mirror.

6. The device according to claim 1, wherein the light source is a laser light source and the light beam is a laser light.

7. The device according to claim 1, wherein the device further comprises attachment means for attaching the device onto a bicycle.

8. The device according to claim 1, wherein the projected image is a marker.

9. The device according to claim 8, wherein the detected activity related parameter is a speed of the device and the marker indicates the speed of the device.

10. The device according to claim 8, wherein the detected activity related parameter is a heart rate and wherein the processor is configured to create the information based on the heart rate.

11. The device according to claim 10, wherein the marker indicates the heart rate.

12. A system for generating a projected image based on an activity related parameter, the system comprising:
a processor configured to determine the activity related parameter;
the processor configured to convert the determined activity related parameter into an image; and
a device for projecting the image onto a ground surface outside the device;
the device comprising:
a light source for emitting a light beam from the device to project the image onto the ground surface; and
at least a first actuator for adjusting a relative direction of the light beam towards the ground surface with respect to an orientation of the device relative to the ground surface,
wherein a distance between the device and a position of the projected image on the ground surface is a function of the determined activity related parameter and the projected image is a marker of light rendered on the ground surface at a distance from the device, which marker of light is rendered on the ground surface further away from the device if the activity related parameter is low and closer to the device if the activity related parameter is high.

13. The system according to claim 12, wherein the processor is a portable computing device coupled to at least one parameter measurement sensor.

14. The system according claim 12, wherein the system further comprises a processing device for determining a velocity vector of the device.

15. The system according to claim 12, wherein the system further comprises a bracket for attaching the device to a bicycle.

16. The system according to claim 12, wherein the system further comprises means for attaching the device to an ear of the user.

17. The system according to claim 12, wherein the image projected on the ground surface is a marker.

18. The system according to claim 17, wherein the device is connected to a vehicle, the determined activity related parameter is a velocity of the vehicle, and the marker indicates the velocity of the vehicle.

19. The system according to claim 17, wherein the determined activity related parameter is a heart rate and the marker indicates the heart rate.

20. The system according to claim 12, wherein the determined activity related parameter includes one or more of a detected speed of the device or a heart rate associated with a user of the device.

* * * * *